Figure 1:
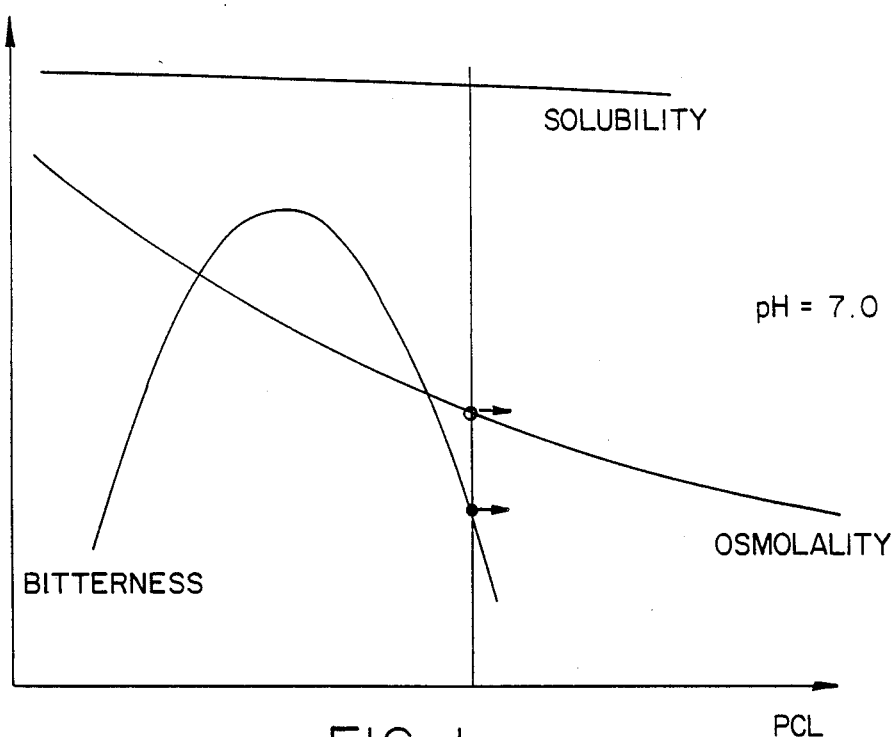

United States Patent [19]

Frokjaer et al.

[11] Patent Number: 4,959,350

[45] Date of Patent: Sep. 25, 1990

[54] ENTERAL DIET PRODUCT AND AGENT FOR PRODUCTION THEREOF

[75] Inventors: Sven Frøkjaer, Naerum; Svend Eriksen, Alleroed; Jens L. Adler-Nissen, Hellerup, all of Denmark

[73] Assignee: Novo Industri A/S, Bagsvaerd, Denmark

[21] Appl. No.: 38,668

[22] Filed: Apr. 15, 1987

[30] Foreign Application Priority Data

Apr. 21, 1986 [SE] Sweden ............................ 8601828

[51] Int. Cl.$^5$ .......................... A23J 1/14; A61K 37/18
[52] U.S. Cl. ........................................ 514/2; 426/656; 514/21; 530/378
[58] Field of Search .............. 514/2; 530/378; 524/21; 426/656

[56] References Cited

U.S. PATENT DOCUMENTS

| | | | |
|---|---|---|---|
| 4,091,120 | 5/1978 | Goodnight, Jr. et al. | 530/378 |
| 4,309,417 | 1/1982 | Staples | 514/21 |
| 4,497,800 | 2/1985 | Larson et al. | 426/656 |
| 4,690,820 | 9/1987 | Simko | 514/2 |

OTHER PUBLICATIONS

V. B. Tolstoguzor et al., J. Dispersion Science and Technology, 6 (5), 575–603 (1985).

*Primary Examiner*—Howard E. Schain
*Assistant Examiner*—Choon P. Koh
*Attorney, Agent, or Firm*—Morris Fidelman; Franklin D. Wolffe

[57] ABSTRACT

An enteral diet composition which comprises a balanced diet aqueous medium mixture of fat, carbohydrate, and dietary nitrogen compounds characterized by a total energy content of at least about 0.68 kcal/ml, an osmolality of below about 350 milli-osmol and a pH lower than about 4.5. The dietary nitrogen compounds are at least about 95% soluble in the aqueous medium and are free from bitterness in the composition. At least about 50% of the dietary nitrogen compounds is derived from vegetable protein source(s).

The enteral diet product exhibits a combination of advantageous characteristics, i.e., good microbiological stability, good physical stability of the emulsion, low osmolality, satisfactory organoleptic properties, and satisfactory nutritional and handling properties.

11 Claims, 1 Drawing Sheet

ENTERAL DIET PRODUCT AND AGENT FOR PRODUCTION THEREOF

SUMMARY

The invention relates to an enteral diet product with a pH lower than about 4.5 and comprising water, fat, and dietary nitrogen compounds, the last being derived from proteins.

In this specification, an "enteral diet product" is intended to mean either a diet product intended for peroral administration or a diet product intended for introduction gastrointestinally by means of a tube. The preferred use of the enteral diet product is for peroral purposes, as the taste of the product is an important aspect of the invention, as will later be elucidated, but the enteral diet product according to the invention can also be administered gastrointestinally, if desired.

Enteral diet products with a pH value above about 4.5 are outside the scope of the invention, as such products are not microbially stable unless sterilized.

BACKGROUND OF THE INVENTION

A prior art enteral diet product is described in U.S. Pat. No. 4,497,800 (Mead Johnson) which teaches a nutritionally complete ready-to-use liquid diet for providing total patient nourishment. Although this prior art enteral diet product exhibits several advantages, e.g., a pH below around 4.5, which provides for microbial stability, it also exhibits some drawbacks notably, a too high osmolality, (which gives rise to a high osmotic load on the patient, and on occasion, poor palatability and diarrhea) and the necessity for inclusion of a separate emulsifier in order to generate a physically stable emulsion. Just to demonstrate that formulations of enteral diet products face multiple complex problems, it is noted that correction of the high osmolality in the products described by U.S. Pat. No. 4,497,800 through replacement of some of the amino acids with a protein derived product containing longer peptide chains may very well lead to a bitter tasting product, one unacceptable organoleptically.

Another prior art enteral diet product is described in European Patent Application No. 0,126,666 (Roussel-Uclaf), which teaches a diet product, the nitrogen part of which is a specified mixture of peptides of animal origin. However, the organoleptic properties of this prior art product are not believed to be satisfactory due to bitter taste.

Thus, a need exists for an enteral diet product of a pH value lower than about 4.5 and comprising as dietary nitrogen compounds protein derived compounds, fat, carbohydrate and water, which besides possessing the character of a physically and microbially stable emulsion should possess a satisfactory low osmolality, satisfactory organoleptic properties and satisfactory nutritional and handling properties in the clinic. The enteral diet products of the present invention exhibit all of the above-listed desired characteristics and properties.

BRIEF STATEMENT OF THE INVENTION

Briefly stated, an enteral diet composition of this invention comprises a balanced diet aqueous medium mixture of fat, carbohydrate, and dietary nitrogen compounds having a total energy content of at least about 0.68 koal/ml, and exhibiting an osmolality of below about 350 milli-osmol and a pH lower than about 4.5, the dietary nitrogen compounds being at least about 95% soluble in aqueous media. The composition is characterized by an absence of bitterness. At least about 50% of the dietary nitrogen compounds is derived from vegetable protein source(s).

The fat and carbohydrate components in the dietary compositions of this invention may be the same as have been employed heretofore. On an energy basis, the amount of fat (triglycerides) is 3-60% of the composition, the amount of dietary nitrogen compounds is 10-35% of the composition and carbohydrates are the balance.

As is pointed out in detail hereinafter, the vegetable protein source nitrogen compounds in the compositions of this invention are within a relatively narrow window of suitable physical properties and acceptable taste that has been found to exist at the sought after pH 4.5 and lower.

BRIEF DISCUSSION OF THE INVENTION AS A WHOLE

Figure 2:
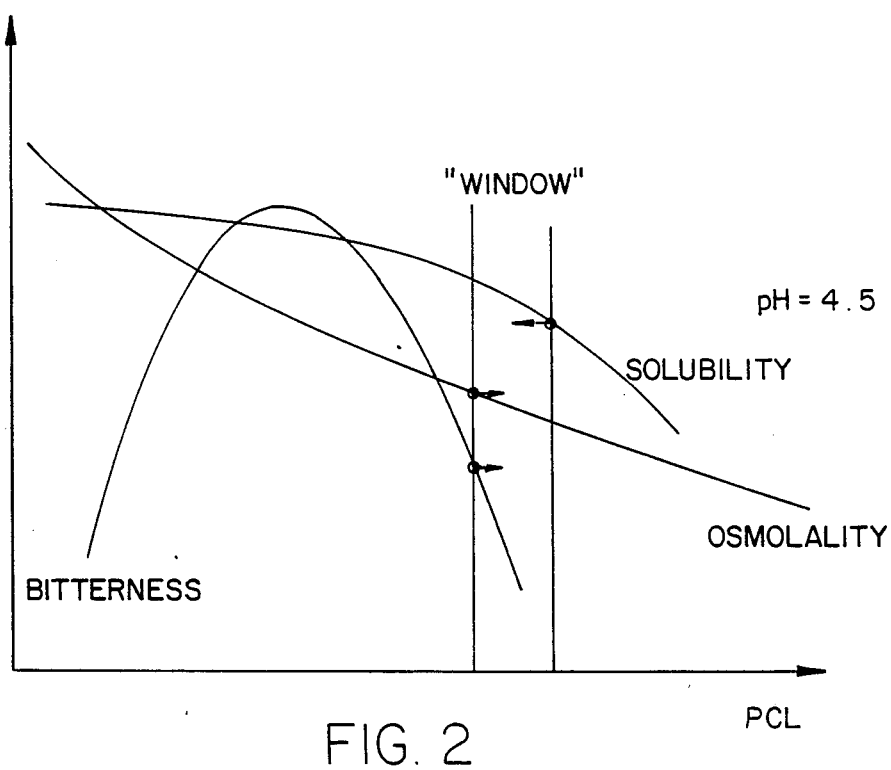

For further understanding of this invention, reference is made to the attached drawing wherein:

FIG. 1 constitutes a schematic plot of bitterness, nitrogen solubility and osmolality against peptide chain length at pH 7; and FIG. 2 constitutes a schematic plot of bitterness, nitrogen solubility and osmolality against peptide chain length at pH 4.5.

It may be seen that at pH solubility of the peptide is not materially affected by peptide chain length. The limiting factors on peptide chain length for acceptability in enteral diet compositions are osmolality and bitterness. In general, peptides to the right of the arrows on FIG. 1 should be acceptable. However, enteral diet compositions of pH 7.0 suffer from a taste disadvantage, in that many persons tire of their bland creamy taste, preferring the tart or acidic taste of lower pH compositions. Unfortunately, the pH of many, if not all, prior art pH 7 liquid diet compositions cannot readily be lowered, say to pH 4.5. Their peptide content becomes at least partially insoluble.

It has been found that hydrolyzed vegetable proteins exhibit a substantial degree of solubility at pH 4.5. Moreover, some of the peptides soluble at pH 4.5 are also acceptable organoleptically i.e., non-bitter and in osmolality; see the solubility curve shown in FIG. 2. Thus, a peptide chain length range exists, a window so to speak, of peptides suitable for a pH 4.5 enteral diet composition. This relatively narrow peptide chain length window is illustrated in FIG. 2 by the arrows and parallel lines. Peptides of chain length to the right of the bitterness arrow and osmolality arrow, and to the left of the solubility arrow are suitable.

It should be appreciated that FIG. 2 is a schematic representation of the relation between peptide chain length and the functional properties of the peptide. The window may be wider or narrower than illustrated. The window size and location along the PCL line will vary according to the particular vegetable protein source for the peptides and/or with the relative proportion in the enteral diet of vegetable protein origin nitrogen compounds and animal protein origin (e.g., casein, whey, gelatine) nitrogen compounds in the enteral diet composition. Suffice it to appreciate that the functional characteristics of low bitterness, acceptable osmolality, and solubility in aqueous media at pH 4.5 are characteristic properties of particular chain length peptides. Of course, the functional characteristics of the peptides relate directly to their use as some, or all of the dietary nitrogen compounds in an enteral diet product and, therefore, the nitrogen compounds will be described hereinafter in terms of their functional properties and measurements therefor (rather than according to amino acid content and peptide chain lengths).

DETAILED DISCUSSION OF THE INVENTION

To recapitulate, the enteral diet product according to the invention is of a pH lower than about 4.5 and comprising dietary nitrogen compounds, fat, carbohydrate and water. The dietary nitrogen compounds are of a nonbitter nature in conjunction with the other constituents of the enteral diet product. Also, the dietary nitrogen compounds are soluble in aqueous media between pH 2-7, at least according to the solubility test described hereinafter. At least 50% of the dietary nitrogen compounds is of vegetable (protein) origin. The osmolality of the enteral diet product is below 350 milliosmol, and the total energy content of the enteral diet product is at least 0.68 koal/ml.

Surprisingly, it has been found that no emulsifier need be added to the product. The excellent emulsion properties of the product according to the invention may originate from the special category of vegetable source nitrogen compounds which forms part of the enteral diet product.

Bitterness

The dietary nitrogen compounds should be of a non-bitter nature when present in combination with the other constituents of the enteral diet product. Even if some of the dietary nitrogen compounds per se are bitter to a certain degree, the decisive requirement is that they are not bitter in conjunction with the other constituents of the enteral diet product. Thus, a zero, or near-to-zero level of bitterness is not required for the product according to the invention, or for that matter, for prior art enteral diet products.

The bitter off-taste of protein hydrolyzates is a much studied field, vide e.g., Adler-Nissen (1985) "Relationship of Structure to Taste of Peptides and Peptide Mixtures", in "Protein Tailoring and Reagents for Food and Medical Uses," (Feeny, R. E., Whitaker, J. R., eds.), Maroel Dekker, Inc., New York. Thus, it is known that bitterness is caused by the presence of oligopeptides with a high content of hydrophobio amino acids. These oligopeptides may be degraded by exopeptidases, but the resulting osmolality will be too high due to the formation of large amounts of free amino acids, vide e.g., British Patent No. 1,338,936. However, the art knows how to obtain a protein hydrolyzate which is non-bitter in conjunction with the other constituents of the enteral diet product.

In this regard, reference can be made to U.S. Pat. No. 3,876,806 which describes a polypeptide of low bitterness and to U.S. Pat. No. 4,100,024 (Adler-Nissen), which describes critical parameters for production of non-bitter protein hydrolyzates including proportion between enzyme activity and soy substrate, pH and degree of hydrolysis. For the sake of brevity, reference herein to a DH controlled protein hydrolysis may be taken to refer to the process described in U.S. Pat. No. 4,100,024. Additional process steps known per se, as a flashing to remove soy bean volatiles and a hyperfiltration or electrodialysis to remove ions, may be incorporated into the process; however, they do not contribute to the lowering of the level of peptide bitterness.

The nitrogen compounds need not be of some particular vegetable protein origin. Any dietary nitrogen compounds which are of a non-bitter nature (in conjunction with the other constituents of the enteral diet product), and which comply with the requirements of osmolality and solubility are suitable for practice of the invention. With a DH controlled protein hydrolysis, but substituting faba bean protein or sesame seed protein for the soy bean protein described in U.S. Pat. No. 4,100,024, an excellent, non-bitter protein hydrolyzate can be produced. In regard to faba bean protein, reference is made to Olsen, H. S., "A Survey on Recent Developments in Industrial Developments of Vicia Faba Protein" in "Vicia Faba. Feeding Value, Processing and Viruses," (Bond, D. A., ed.) ECSC, EEC, EAEC, Bruxelles, 1980, pp. 233-255.

It goes without saying, that the dietary nitrogen compounds should be selected in such a manner that a balanced amino acid diet is obtained. Just to mention an example, some cereal proteins, e.g., corn, wheat and oats are lysine deficient and, thus, not suited as sole sources of dietary nitrogen. On the other hand, proteins originating from leguminous plants, e.g., soy or peas, are well suited for use alone in the dietary product.

Solubility

The dietary nitrogen compound should be soluble in aqueous media between pH 2-7 at least according to the solubility test carried out as indicated below (see "J. Adler-Nissen and H. Sejr Olsen, ACS Symposium Series, No. 92, "Functionality and Protein Structure," 1979, pp. 128-129).

Solubility of the samples determined over a pH range of 2.0-9.0 in a 1% protein dispersion in 0.2M NaCl by the following procedure:

2.0 g of protein product is dispersed in 150 ml of 0.2M NaCl using a laboratory blender for 2 minutes. The blender is washed with 50 ml of 0.2M NaCl and the washing liquid combined with the homogenized sample. pH is adjusted with 0.2M HCl or 0.2M NaOH and the dispersion stirred with a magnetic stirrer for 45 minutes. pH is regularly adjusted, if necessary. At the end of the stirring period, the volume is determined by weighing and 25 ml of the dispersion is centrifuged at 5000 x g for 30 minutes. The supernatants are analyzed for nitrogen content by the Kjeldahl procedure (double determination), and the nitrogen solubility calculated as (soluble N%/total N%).

The dietary nitrogen compound is considered soluble in aqueous media between pH 2-7 in the sense of this invention, if the nitrogen solubility according to the above test exceeds 95%.

Reference is made to page 134 in the above-cited Adler-Nissen et al paper from which it appears that the nitrogen solubility of unseparated soy hydrolysates for a DH of around 8.0 is around 80% for a hydrolysis carried out at pH 8.0, and that the nitrogen solubility increases with increasing DH values. These relationships are very dependent on the protein source. Except for whey protein, all of the dietary nitrogen compounds used in the enteral diet product, according to the invention, have to be composed mainly of medium chain length polypeptides: if the chain is too long, the peptides will not be soluble and if they are too short, problems in relation to osmolality and physical stability of the emulsion will arise. A small amount of free amino acids may be present, but not too much since free amino acids generate high osmolality.

At least 50% of the dietary nitrogen compounds in the enteral diet products of the invention is of vegetable origin. It has been found that the organoleptic requirements for the products are best fulfilled in this fashion, and moreover, makes possible relatively cheap enteral diet products with optimally balanced amino acid compositions.

Osmolality

The osmolality of the enteral diet product should be below about 350 milli-osmol in order to prevent the clinical disadvantages attached to a diet produced with an osmolality above around 350 milli-osmol.

The limit of 350 milli-osmol corresponding roughly to 50–80 milli-osmol above the normal physiological level is not critical in the sense that the disadvantages associated to a high osmolality appear abruptly at an osmolality just above 350 milli-osmol, but rather they appear gradually and become more and more pronounced, with higher osmolality levels.

The contribution from the dietary nitrogen to the total osmolality can be predicted by means of the below indicated Equation (1):

$$\Delta C = 100/(100 - D\%) \times P \times \phi \times 8/PCL \text{ milli-osmol} \quad (1)$$

where:
$\Delta C$ is the contribution to the total osmolality.
D is the weight per cent dry matter concentration of the final enteral diet product.
P is the protein content in g per kg.
$\phi$ is the osmotic coefficient of peptides and amino acids; this has been found to be around 0.96 for topical values of pH and protein concentrations (Adler-Nissen, J. (1984), Control of the Proteolytic Reaction and the Level of Bitterness in Protein Hydrolysis Processes. J. Chem. Technol. Biotechnol. 34B, 215–222).
PCL is the number average peptide chain length in amino acid residues. PCL can be estimated by means of Equation (2):

$$PCL = 8/(\text{leu-NH}_2 - \text{e-NH}_2)$$

where:
leu-NH$_2$ is the concentration of free amino groups in leucine amino equivalents per kg protein as measured by the TNBS-reaction (Adler-Nissen, J. (1979), Determination of the degree of hydrolysis of food protein hydrolyzates by trinitrobenzenesulfonic acid. J. Agric. Food Chem. 27, 1256–1262).
e-NH$_2$ is the concentration of lysine (i.e. epsilon amino groups) in the same units as above indicated.

The factor 8, which appears in both equations, is based on the fact that most food proteins contain approximately 8 mole amino acids per kg (Adler-Nissen, 1984, previously cited).

If the protein hydrolyzate contains a known percentage of free amino acids, denoted %AA, a maximum value of PCL can be calculated from equation (3):

$$PCL_{max} = 100/\%AA$$

Equation (3) is useful for a quick determination of the minimum contribution to the total osmolality since the percentage of free amino acids in many enteral diet products is often known from the description of the product.

Osmolality has been discussed at some length because osmolality problems can arise when products according to the invention are formulated. The relatively flat osmolality curve on FIGS. 1 and 2 may be deceptive in this regard. The entire window illustrated in FIG. 2 is relatively near the 350 milli-osmol value, limiting then the proportion of free amino acids which should be in the enteral product. Many prior art enteral diet product exhibit an osmolality exceeding 350 milli-osmol.

To illustrate the osmolality problems related to a considerable amount of free amino acids in an enteral diet product, the osmolality originating from the dietary nitrogen in the preferred embodiment of the formulation disclosed in the previously mentioned Mead Johnson patent is calculated in the following:

D % = about 23%; P = 45 g/kg; % AA = about 70% — which inserted in above equations (3) and (1) gives a minimum value of $\Delta C$ = 314 milli-osmol. Since also the carbohydrate and the minerals contribute significantly to the osmolality, the resulting total osmolality of the enteral diet product would be considerably above the normal physiological level of 270–300 milli-osmol in the body fluids.

General Discussion

Finally the total energy content of the enteral diet product should be at least 0.68 kcal/ml. This figure corresponds to the energy content of whole cow's milk and thus this requirement secures that the patient only needs to drink a relatively small volume of enteral diet product per day, far less than a volume objectionable to the patient.

In order to illustrate the complex relations in enteral diet products between osmolality, solubility and bitterness versus the average peptide chain length (PCL) of the protein hydrolysate in question, reference is again made to FIGS. 1 and 2 and the following, more detailed explanation is offered.

Osmolality

Since osmolality decreases with increasing PCL a minimum PCL value exists below which the osmolality of the protein hydrolyzate will exceed an acceptable value.

Solubility

For increasing values of PCL solubility of protein hydrolyzate will be dependent on the pH of the product. At neutrality the solubility will remain high whereas the solubility at around the isoelectric point (~pH 4.5) will start to decrease for a given PCL. This decrease will continue with increasing PCL, meaning that a maximum PCL value exists where 95% of the protein will be in solution.

Bitterness

The bitterness curve in relation to PCL demonstrates that a range of PCL values exists where bitterness is prohibitive for acceptance of the final product, i.e., acceptable PCL values must either be above or below this range.

For each peptide at a given pH, a range of PCL values representing a compromise with low osmolality, high solubility and low or acceptable bitterness exists. This range will be situated to the right of the maximum for bitterness, and at pH values below 4.5, this range will be a "window" upwardly limited by the solubility of the protein in question. The existence of such "window" to the right of the maximum for bitterness, in relation to enteral diet products with a pH of 4.5 or below, could not be predicted and is surprising. The prior art diet products known to the inventors hereof are not within this window.

Thus, DE-OS 2844861 describes a dietary nutrient for oral use; however, this nutrient has a pH around neutrality.

Furthermore, DE-OS 2751024 describes a method for production of a nutrient based on soy protein. However, this nutrient is not soluble at all pH values between 2 and 7, and also it exhibits a pH value above 4.5.

Furthermore U.S. Pat. No. 4.483.874 describes a preparation of a milk substitute. If reformulated into an enteral diet product this product would possess an osmolality far above 350 milliosmol, and also the organoleptic properties of the product would be unsatisfactory.

Furthermore, European patent application with publication no. 0 150 053 describes a hydrocaloric low osmotic aqueous preparation for infusion. This product is parenteral, and also the pH thereof is far above 4.5.

Furthermore, DE-OS 2457733 describes a fluid nutrient for newborn babies. This nutrient does not contain protein or fat, and the pH thereof is above 4.5.

U.S. Pat. No. 4.100.024 and 3.876.806, to which reference has already been made, describe a protein hydrolyzate, which may be used as the protein fraction of the enteral diet product according to the invention. It is also described that a simple drink with pH 4.5 can be produced on the basis of this protein hydrolyzate; this drink, however, does not contain fat and exhibits an osmolality far above 350 milliosmol.

Finally, U.S. Pat. No. 4.259.358 describes food ingredients and foods for human use. However, all described food ingredients and foods exhibit a pH above 4.5.

In a preferred embodiment of the product according to the invention at least 75% of the dietary nitrogen compounds is of vegetable origin.

In a more preferred embodiment of the product according to the invention at least 90% of the dietary nitrogen compounds is of vegetable origin. In this manner a cheap and yet satisfactory product is obtained.

In a preferred embodiment of the product according to the invention the dietary nitrogen compounds of vegetable origin are fully or partially from soy. Soy protein is an easily available and very cheap nitrogen source.

In a preferred embodiment of the product according to the invention the dietary nitrogen compounds of vegetable origin are partially from soy, and also include nitrogen compounds originating from faba beans, rape seed, oats, sesame, or peas. In this way it is possible to obtain a product with nitrogen compounds, which are extraordinarily well balanced in regard to amino acid composition. This will be elucidated further later in this specification, i.e. in relation to the product C described just before the examples.

In a preferred embodiment of the product according to the invention the dietary nitrogen compounds of vegetable origin are produced by means of a DH controlled protein hydrolysis. In this manner a product with extraordinarily good organoleptic properties is obtained.

In a preferred embodiment of the product according to the invention the total energy of the product is between 0.70 and 2.00 kcal/ml. In this manner a sound compromise between viscosity and energy content can be obtained.

In a preferred embodiment of the product according to the invention on an energy basis the amount of dietary nitrogen compounds is 10 to 35%, the amount of fat is 3 to 60%, the residual amount of energy originating from carbohydrate. In this manner the nutritional demand can be fully met.

In a preferred embodiment of the product according to the invention the product also contains additives usually present in enteral diet products, including flavoring agents, sweetening agents, minerals, trace elements, vitamins, and electrolytes. In this manner all nutritional and organoleptic demands can be met.

In a preferred embodiment of the product according to the invention the product contains a minor amount of an anionic polysaccharide, preferably between 0.05 and 1.0% by weight. The usual emulsified enteral diet product according to the invention (i.e. without anionic polysaccharide is stable for several days, showing no or only very weak tendencies of coalescence. Some creaming might occur, but after simple stirring with a spoon, the liquid is again homogenous in appearance and suitable for drinking. However, improved stability against creaming can be obtained by addition of small amounts of an anionic polysaccharide. Reference is made to V. B. Tolstoguzov and E. E. Braudo, Proteins and Anionic Polysaccharides as Stabilizers of o/w Emulsions, J. Dispersion Science and Technology, 6(5), 575–603 (1985). Examples of anionic polysaccharides are pectin, xanthan gum and sodium alginate.

In a preferred embodiment of the product according to the invention the anionic polysaccharide is pectin, preferably a highly methoxylated pectin, which even in small concentrations provides an extraordinarily good improved stability against creaming.

Also, the invention comprises just a powder mixture of the solid components of the enteral diet product. The enteral diet product as such can be produced by simple mixing of the solid components mixture with water in such ratio that the total energy content of the product is at least 0.68 kcal/ml.

In order to illustrate the enteral diet product according to the invention against a background of prior art enteral diet products, reference is made to the following Table 1, which is a tabulation of properties of prior art enteral diet products versus properties of a preferred embodiment of enteral diet product according to the invention.

TABLE 1

| Enteral diet product | Major protein source (g/l) | Major fat source (g/l) | Major carbohydrate source (g/l) | Energy content kcal/ml | Osmolality mOsm/kg | pH, measured |
| --- | --- | --- | --- | --- | --- | --- |
| Ensure | Caseinates, soy protein isolate (37.2) | Corn oil (37.2) | Hydrolyzed corn starch, sucrose (145) | 1.0 | 450 | 6.6 |

TABLE 1-continued

| | Enteral diet product | Major protein source (g/l) | Major fat source (g/l) | Major carbohydrate source (g/l) | Energy content kcal/ml | Osmolality mOsm/kg | pH, measured |
|---|---|---|---|---|---|---|---|
| | Nutridrink | Caseinates (50) | Veg. oil (65) | Maltodextrins, sucrose (179) | 1.5 | 470 | 6.6 |
| | Isocal | Caseinates soy/protein isolate (34) | MCT*, corn oil, soy oil (44) | Maltodextrins (133) | 1.0 | 300 | 6.5 |
| | Peptosorbin | Hydrolyzed lactalbumin (45) | MCT*, sunflower oil (13.3) | Hydrolyzed corn starch (175) | 1.0 | 400 | 7.3 |
| Prior art | Reabilan | Hydrolyzed whey protein and casein (31.5) | MCT*, veg. oil (39) | Maltodextrins, starch (131.5) | 1.0 | 300 | 6.6 |
| | Vivonex T.E.N. | Free amino acids (38) | Safflower oil (3.0) | Maltodextrins, modified starch (206) | 1.0 | 630 | 5.3 |
| | Criticare HN | Hydrolyzed casein, free amino acids (38) | Safflower oil (3) | Maltodextrins, modified corn starch (222) | 1.0 | 650 | 4.5 |
| Invention | NOVO Enteral Diet Product according to example no. 5 a | Hydrolyzed soy protein (50) | MCT*, soy oil (36) | Maltodextrins (119) | 1.0 | 270 | 4.3 |

*MCT = Medium Chain Triglycerides

As appears from Table 1, none of the commercial products exhibited a pH value below 4.5. If the pH value of the known product Isocal or other casein-based products is lowered below 4.5, a heavy precipitation occurs, and if the pH value of the known product Reabilan is lowered below 4.5, the organoleptic properties thereof are unacceptable. Table 1 illustrates that the enteral diet products, according to the invention, differ substantially from the prior art enteral diet products.

The invention will be illustrated by the following Examples 1-9, whereby all Examples illustrate the enteral diet product according to the invention, and whereby Example 6 also illustrates a solid form mixture according to the invention suited for production of the enteral diet product as such. Examples A-F describe preparation of the dietary nitrogen compounds employed in the Examples 1-9.

Also, subsequent to Example 9, a table, i.e., Table 2, is provided which tabulates some important characteristics of the products made according to Examples 1-9. The bitterness test listed in Table 2 was carried out by a trained taste panel consisting of six persons, utilizing the triangle test.

PRODUCT A

Preparation of Protein Hydrolyzate

Protein hydrolyzate from soy was produced according to U.S. Pat. No. 4,100,024 example 2, except that hydrochloric acid was used instead of citric acid for inactivation of the enzyme. To improve flavor the supernatant is heated to 140° C. for 2-4 seconds and then flashed into a vacuum chamber. The product is further desalinated according to H. Sejr Olsen and Adler-Nissen, Application of Ultra- and Hyperfiltration during production of enzymatically modified proteins, ACS Symp. Ser. 154, 133-169.

PRODUCT B

By use of defatted sesame meal as a starting material a protein hydrolyzate was produced according to U.S. Pat. No. 4,100,024, example 2, except that hydrochloric acid was used instead of citric acid for inactivation of the enzyme.

PRODUCT C

Protein hydrolyzates produced by various mixtures of products A and B in different ratios were prepared, and the predicted biological value was calculated in each case according to Mørup and Olesen, Nutrition Reports International 13 (1974) 355-65 based upon the amino acid analyses.

| | Amino acid analysis (g/16 g N) | |
|---|---|---|
| | Hydrolyzate from | |
| A.A. | Soy (Product A) | Sesame (Product B) |
| Apartic acid | 12.4 | 7.3 |
| Threonine | 3.8 | 2.5 |
| Serine | 5.0 | 3.9 |
| Glutamic acid | 20.6 | 22.0 |
| Proline | 5.0 | 3.4 |
| Glycine | 4.0 | 4.7 |
| Alanine | 4.5 | 4.1 |
| Valine | 4.6 | 4.0 |
| Isoleucine | 4.4 | 3.2 |
| Leucine | 6.5 | 6.0 |
| Tyrosine | 2.5 | 2.8 |
| Phenylalanine | 4.0 | 3.8 |
| Lysine | 6.7 | 3.0 |
| Histidine | 2.4 | 2.2 |
| Arginine | 6.7 | 17.4 |
| Cystine | 1.9 | 2.5 |
| Methionine | 1.1 | 2.2 |
| Tryptophan | 0.5 | 1.3 |

Product C is the product indicated in the below table with the highest PV value.

| Predicted biological value (PV) of protein mixtures | |  |
|---|---|---|
| Soy:Sesame | PV | |
| 100:0 | 72 | |
| 80:20 | 95 | |
| 67:33 | 104 | Product C |
| 60:40 | 104 | |
| 50:50 | 98 | |
| 33:67 | 80 | |
| 20:60 | 62 | |
| 0:100 | 44 | |

PRODUCT D

As product A, but with a DH value of 15%.

PRODUCT E

As product A, but with a DH value of 14%.

PRODUCT F

As product E, but with a pea protein isolate with 88% protein (N×6.25) as a starting material.

EXAMPLE 1

A diet product is prepared according to the following formula:

| Composition for 100 ml | |  |
|---|---|---|
| Protein: Product D (N × 6.25) | 5.00 | g |
| Carbohydrate: Maltodextrins MD01 (Rochette Freres) | 11.89 | — |
| Fat: Medium chain triglyceride viscoleo (Dansk Soja-kagefabrik) | 2.98 | — |
| Soy bean oil | 0.59 | — |
| Water ad | 100 | ml |

For the preparation of one liter of product the procedure is as follows:

| | Constituents | | |
|---|---|---|---|
| I | Tricalcium dicitrate | 0.750 | g |
| | Citric acid | 1.750 | — |
| | Potassium citrate | 1.000 | — |
| | Aspartame | 0.240 | — |
| | Ascorbic acid | 0.100 | — |
| II | Product D (N × 6.25) | 50.0 | g |
| III | Maltodextrin MD01 | 118.9 | g |
| | Demineralized water | 400 | ml |
| IV | Viscoleo | 29.8 | g |
| | Soy bean oil | 5.9 | — |
| V | Demineralized water ad | 1000 | ml |

PRODUCTION PROCEDURE

I is dissolved in II. pH is measured to pH=4.3. Maltodextrin is dissolved in water by heating to 50° C. (III). III is mixed with I+II and IV is added. Finally water (V) is added to a total volume of 1000 ml. The product is homogenized on a low pressure homogenizer, Gaulin HS 1. The product is filled in a suitable package and stored at 4° C.

For the preparation of one thousand liters of a similar, enriched product the procedure is as follows:

| | Constituents | | |
|---|---|---|---|
| I | Tricalcium dicitrate | 750 | g |
| | Citric acid | 1750 | — |

| | Constituents | | |
|---|---|---|---|
| | Potassium citrate | 1000 | — |
| | Aspartame | 240 | — |
| | Ascorbic acid | 100 | — |
| II | Product D in an amount corresponding to 50 kg N × 6.25 | 50.0 | kg protein |
| III | Maltodextrin MDO1 | 118.9 | kg |
| | Demineralized water | 400 | l |
| IV | Viscoleo | 29.8 | kg |
| | Soy bean oil | 5.9 | kg |
| V | Demineralized water ad | 1000 | l |

PRODUCTION PROCEDURE

I is dissolved in II. The pH value was 4.3. Maltodextrin is dissolved in water by heating to 50° C. (III). III is mixed with I+II and IV is added. Finally water (V) is added to a total volume of 1000 l. The product is prehomogenized on a low pressure homogenizer, pasteurized at 85° C. for 4 seconds and finally homogenized at a pressure around 200 kg/cm² at a temperature of 60° C. The pasteurized/homogenized product is collected in a sterile storage tank. The product is filled in a suitable package under aseptic conditions and stored at 4° C.

The droplet size distribution of the fat globules was measured by means of a Coulter Counter and appears from the below indicated table, in which all sizes are given in μm.

| 90% | 0.92 |
|---|---|
| 80% | 0.97 |
| 70% | 1.02 |
| 60% | 1.07 |
| 50% | 1.12 |
| 40% | 1.17 |
| 30% | 1.23 |
| 20% | 1.3 |
| 10% | 1.41 |

The mean droplet diameter is 1.1 μm, and no droplet with a diameter of less than 0.8 μm could be detected.

Stability: No creaming or coalescence is observed after 24 h.

For further analytical data, vide Table 2.

EXAMPLE 2

A diet product is prepared as in example 1 except that the dietary nitrogen compounds of vegetable origin is only partially on soy basis.

| Composition for 100 ml | | |
|---|---|---|
| Protein: Product C (N × 6.25) | 5.00 | g |
| Carbohydrate: | | |
| Maltodextrins | 11.89 | — |
| Fat: | | |
| Medium chain triglyceride | 2.98 | — |
| Soy bean oil | 0.59 | — |
| Water ad | 100 | ml |

For analytical data, vide Table 2.

EXAMPLE 3(a)

A diet product is prepared as in example 1 except that the dietary nitrogen compounds are replaced by whey protein/product E in a ratio of 1:1 on an N×6.25 basis.

For analytical data, vide Table 2.

EXAMPLE 3(b)

A diet product is prepared as in example 1 except that the dietary nitrogen compounds are replaced by whey protein/product E in a ratio of 40:60 on a N×6.25 basis.
For analytical data, vide Table 2.

EXAMPLE 3(c)

A diet product is prepared as in example 1 except that the dietary nitrogen compounds are replaced by whey protein/product E in a ratio of 25:75 on a N×6.25 basis.
For analytical data, vide Table 2.

EXAMPLE 4

A diet product is prepared as in example 1 except that the dietary nitrogen compounds are supplemented with free amino acids to improve the biological value.

| Composition for 100 ml | |
|---|---|
| Proteins: | |
| Product D (N × 6.25) | 5.00 g |
| Methionine | 65 mg |
| Tryptophan | 22 mg |
| Carbohydrate: | |
| Maltodextrins | 11.89 g |
| Fat: | |
| Medium chain triglyceride | 2.98 g |
| Soy bean oil | 0.59 g |
| Water ad | 100 ml |

For analytical data vide Table 2.

EXAMPLE 5(a)

A diet product is prepared as in example 1, except that the product contains a minor amount of pectin.

1000 liter of product is produced according to the production procedure described in example 1 except that 100 l of the amount of water in V is replaced with 100 l of a 2.5% pectin type JM aqueous solution (Københavns Pektinfabrik A/S). Stability: No coalescence and only negligible creaming is observed after 2 months.

For further analytical data vide Table 2.

EXAMPLE 5(b)

A diet product is prepared as in example 1 except that the product contains a minor amount of xanthan gum.

1 liter of the product is produced according to the procedure described in example 1 except that 100 ml of the water in V is replaced with 100 ml 1.0% xanthan gum.
For analytical data, vide Table 2.

EXAMPLE 5(c)

A diet product is prepared as in example 5b except that the 1.0% xanthan gum solution is replaced with 100 ml 2.5% sodium alginate.
For analytical data, vide Table 2.

EXAMPLE 6

A diet product is prepared as in example 1. After pasteurizing and homogenizing the product is spray-dried and agglomerated. Before use, the powder is reconstituted by dispersing in water to a final concentration of 1 kcal/ml. The reconstituted product is physically and chemically identical to the product before drying except for an insignificant broadening of droplet size distribution.

The droplet size distribution of the fat globules in the reconstituted diet product was measured by means of a Coulter Counter and appears from the below indicated table, in which all sizes are given in μm.

| | |
|---|---|
| 90% | 1.54 |
| 80% | 1.78 |
| 70% | 2.03 |
| 60% | 2.32 |
| 50% | 2.67 |
| 40% | 3.13 |
| 30% | 3.8 |
| 20% | 5.11 |
| 10% | 12.43 |

The mean droplet diameter is 2.7 μm, and no droplets with a diameter less than 1.0 μm could be detected. Stability: No coalescence and negligible creaming is observed after 24 h.

For further analytical data, vide Table 2 in which the data pertaining to example 6 refers to the reconstituted product.

EXAMPLE 7

A diet product is prepared as in example 1 except that the amount of fat is reduced to 3% on an energy basis.

| Composition for 100 ml: | |
|---|---|
| Protein: Product E (N × 6.25) | 5.00 g |
| Carbohydrate: Maltodextrins | 20.00 — |
| Fat: Grape seed oil | 0.30 — |
| Water: ad | 100 ml |

For analytical data, vide Table 2.

EXAMPLE 8

A diet product is prepared as in example 1 except that the amount of fat is increased to 60% on an energy basis.

| Composition for 100 ml: | |
|---|---|
| Protein: Product E (N × 6.25) | 5.00 g |
| Carbohydrate: Maltodextrins | 5.00 — |
| Fat: Medium chain triglyceride | 6.80 — |
| Grape seed oil | 0.30 — |
| Water: ad | 100 ml |

For analytical data, vide Table 2.

EXAMPLE 9

A diet product is prepared as in example 1 except that the dietary nitrogen compounds are replaced by product F.
For analytical data, vide Table 2.

TABLE 2

| Example No | pH | non-bitterness | solubility % | % N of vegetable origin | osmolality mOsm/kg | energy content kcal/ml |
|---|---|---|---|---|---|---|
| 1 | 4.23 | yes | 100 | 100 | 274 | 1.0 |
| 2 | 4.07 | yes | 100 | 100 | 348 | 1.0 |
| 3 a | 4.36 | yes | 100 | 50 | 204 | 1.0 |
| 3 b | 4.30 | yes | 100 | 60 | 198 | 1.0 |
| 3 c | 4.23 | yes | 100 | 75 | 218 | 1.0 |
| 4 | 4.19 | yes | 100 | 98 | 269 | 1.0 |
| 5 a | 4.33 | yes | 100 | 100 | 270 | 1.0 |
| 5 b | 4.10 | yes | 100 | 100 | 344 | 1.0 |
| 5 c | 4.11 | yes | 100 | 100 | 345 | 1.0 |

TABLE 2-continued

| Example No | pH | non-bitterness | solubility % | % N of vegetable origin | osmolality mOsm/kg | energy content kcal/ml |
|---|---|---|---|---|---|---|
| 6 | 4.25 | yes | 100 | 100 | 259 | 1.0 |
| 7 | 4.10 | yes | 100 | 100 | 325 | 1.0 |
| 8 | 4.09 | yes | 100 | 100 | 225 | 1.0 |
| 9 | 4.15 | yes | 100 | 100 | 209 | 1.0 |

We claim:

1. In an enteral diet product comprising dietary nitrogen compounds, carbohydrate(s) and water and characterized by a pH lower than about 4.5 and an osmolality below about 350 milli-osmal, the improvement which comprises at least 50% of the dietary nitrogen compounds being a vegetable protein hydrolysate characterized by being at least 95% soluble in aqueous media pH 2–7 and by being non-bitter in the enteral diet product, said product further containing fat and a total energy content of at least about 0.68 k cal/ml.

2. A product according to claim 1 wherein said vegetable protein hydrolysate comprises at least 75% of the dietary nitrogen compounds.

3. A product according to claim 1 wherein said vegetable protein hydrolysate comprises at least 90% of the dietary nitrogen compounds.

4. A product according to claim 1 wherein said vegetable protein hydrolysate is at least in part a soy protein hydrolysate.

5. A product according to claim 4 wherein said vegetable protein hydrolysate is in part a soy protein hydrolysate and in part a protein hydrolysate from faba bean, rape seed, oat, sesame or pea.

6. Product according to claim 1 wherein the total energy of the product is between 0.70 and 2.00 kcal/ml.

7. Product according to claim 1 wherein on an energy basis, the amount of dietary nitrogen compounds is 10% to 35%, the amount of fat is 3% to 60%, the balance being carbohydrate.

8. Product according to claim 1 wherein the product also contains one or more of the following additives: flavoring agents, sweetening agents, minerals, trace elements, vitamins, and electrolytes.

9. Product according to claim 1 wherein the improvement also comprises the presence of between 0.05 and 1.0% by weight of an anionic polysaccharide in the product.

10. Product according to claim 9 wherein the anionic polysaccharide is highly methoxylated pectin.

11. The enteral diet product according to claim 1 in a powder form water free state.

* * * * *

UNITED STATES PATENT AND TRADEMARK OFFICE
CERTIFICATE OF CORRECTION

PATENT NO. : 4,959,350

DATED : September 25, 1990

INVENTOR(S) : Sven Frøkjaer et al.

It is certified that error appears in the above-identified patent and that said Letters Patent is hereby corrected as shown below:

Title Page
Item [19]: "Frokjaer" should read --Frøkjaer--.

Col. 1, line 66, "koal/ml" should read -- kcal/ml --.

Col. 3, line 22, "koal/ml" should read -- kcal/ml --.

Col. 3, line 49, "hydrophobio" should read -- hydrophobic --.

Claim 1, line 24, "k cal/ml" should read -- kcal/ml --.

Signed and Sealed this

Seventh Day of January, 1992

Attest:

HARRY F. MANBECK, JR.

*Attesting Officer*    *Commissioner of Patents and Trademarks*